US00PP35101P2

(12) United States Plant Patent
Hanes

(10) Patent No.: US PP35,101 P2
(45) Date of Patent: Apr. 11, 2023

(54) ***PELARGONIUM* PLANT NAMED 'PEQZ0097'**

(50) Latin Name: ***Pelargonium* interspecific**
Varietal Denomination: PEQZ0097

(71) Applicant: SYNGENTA CROP PROTECTION AG, Basel (CH)

(72) Inventor: Mitchell E. Hanes, Morgan Hill, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/803,646

(22) Filed: Sep. 20, 2022

(51) Int. Cl.
*A01H 5/02* (2018.01)
*A01H 6/42* (2018.01)

(52) U.S. Cl.
USPC ..... Plt./328
CPC ..... *A01H 6/425* (2018.05)

(58) Field of Classification Search
USPC ..... Plt./263.1, 324, 325, 328
See application file for complete search history.

*Primary Examiner* — Karen M Redden
(74) *Attorney, Agent, or Firm* — Dale Skalla

(57) ABSTRACT

A new *Pelargonium* plant named 'PEQZ0097' particularly distinguished by light pink inflorescences that darken with age to dark rose, with single florets, held above dark green foliage, on a spreading-trailing plant.

1 Drawing Sheet

Latin name of the genus and species of the plant claimed: *Pelargonium* interspecific.

Varietal denomination: 'PEQZ0097'.

BACKGROUND OF THE NEW PLANT

The present invention comprises a new *Pelargonium*, botanically known as *Pelargonium* interspecific, and hereinafter referred to by the variety name 'PEQZ0097'.

'PEQZ0097' is a product of a planned breeding program. The new cultivar 'PEQZ0097' has light pink inflorescences that darken with age to dark rose, with single florets, held above dark green foliage, on a spreading-trailing plant.

'PEQZ0097' originates from a hybridization in a controlled breeding program made in August 2017 in a greenhouse in Gilroy, Calif. The female parent was an unpatented plant of *P*. interspecific parentage identified as 'PEIBC1104-IV' with lighter green foliage when compared to 'PEQZ0097'.

The male parent of 'PEQZ0097' was an unpatented, proprietary plant of *P*. interspecific parentage, identified as 'PEIBD1411-IV' with a larger plant habit and more petals per flower when compared to 'PEQZ0097'. The resultant seed was sown in December 2017.

'PEQZ0097' was selected as one flowering plant within the progeny of the stated cross in May 2018 in a greenhouse in Gilroy, Calif.

The first act of asexual reproduction of 'PEQZ0097' was accomplished when vegetative stem cuttings were propagated from the initial selection in March 2018 in a greenhouse in Gilroy, Calif.

BRIEF SUMMARY OF INVENTION

Horticultural examination of plants grown from cuttings of the plant initiated in May 2018 in Gilroy, Calif. and continuing thereafter, has demonstrated that the combination of characteristics as herein disclosed for 'PEQZ0097' are firmly fixed and are retained through successive generations of asexual reproduction.

'PEQZ0097' has not been observed under all possible environmental conditions. The phenotype may vary significantly with variations in environment such as temperature, light intensity, and day length.

A Plant Breeder's Right for this cultivar has not yet been applied for. 'PEQZ0097' has not been made publicly available prior to the effective filing date of this application, notwithstanding any disclosure that may have been made less than one year prior to the effective filing date of this application by the inventor or another who obtained 'PEQZ0097' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

The accompanying photographic drawings show typical flower and foliage characteristics of 'PEQZ0097' with colors being as true as possible with an illustration of this type.

Figure 1:
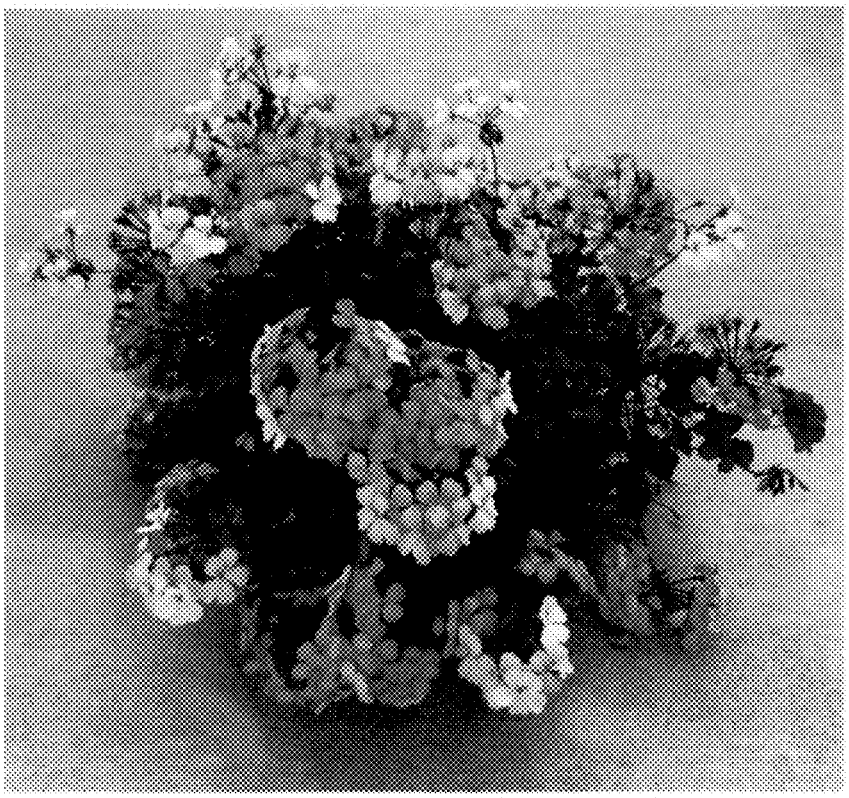
Figure 2:
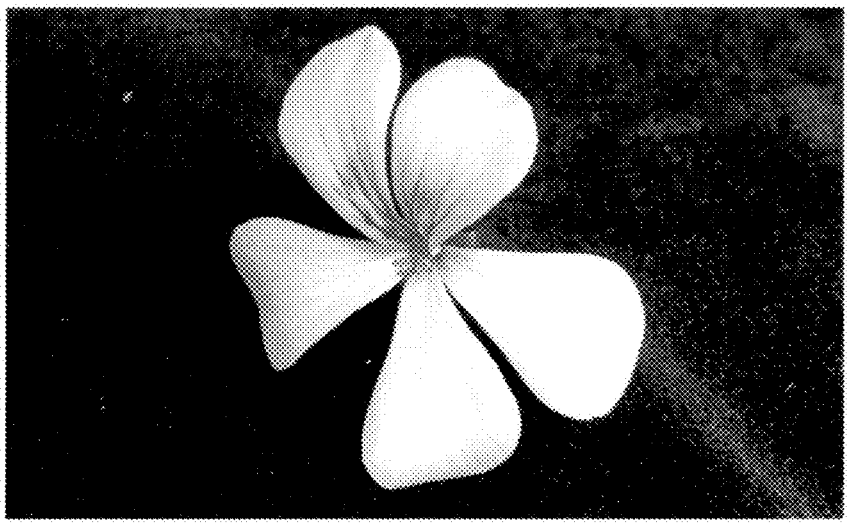

The photographic drawings show in FIG. 1, one flowering plants of the new variety and in FIG. 2, a close-up of an inflorescence.

DETAILED BOTANICAL DESCRIPTION

The plant descriptions and measurements were taken in Gilroy, Calif. in early July 2022 under natural light. These plants were approximately 12 weeks old and were grown in a 12 cm pots, in a greenhouse trial. The plant shown in the photographs weas about 18 weeks old growing in a 23 cm pot in a greenhouse. The photographs were taken in July 2021.

Color references are made to The Royal Horticultural Society Colour Chart (R.H.S.) 2001.

TABLE 1

DIFFERENCES BETWEEN THE NEW VARIETY 'PEQZ0097' AND A MOST SIMILAR VARIETY

| | 'PEQZ0097' | 'CANTE ROS' (U.S. Plant Pat. No. 15,834) |
|---|---|---|
| Color upper petal: | Darkening from light pink to dark pink with age | Stable pink |
| Color of mature leaf: | Dark green | Medium green |

Plant:
- *Form, growth and habit.*—Spreading — trailing.
- *Plant height.*—21-27 cm.
- *Plant height (inflorescence included).*—28-30 cm.
- *Plant width.*—50-59 cm.

Roots:
- *Number of days to initiate roots.*—15-18 days at about 22 degrees C.
- *Number of days to produce a rooted cutting.*—21-23 days at 22 degrees C.
- *Type.*—Fine, fibrous, free branching.
- *Color.*—RHS N155B but whiter.

Foliage:
- *Variegation.*—Absent.
- *Immature leaf, color upper surface.*—Closest to RHS 137C.
- *Immature leaf, lower surface.*—Closest to RHS 138B.
- *Mature leaf, color upper surface.*—Closest to RHS NN137A.
- *Mature leaf, color lower surface.*—Closest to RHS 138B.
- *Length.*—5-7 cm.
- *Width.*—7.5-9 cm.
- *Shape.*—Cordate.
- *Base shape.*—Cordate.
- *Sinus of mature leaf.*—No sinus in mature upper and lower leaf.
- *Leaf base openness.*—Variable, some leaves almost closed, some leaves open or slightly open.
- *Apex shape.*—Acute.
- *Margin.*—Slightly dentate.
- *Texture upper side.*—Hirsute.
- *Texture lower side.*—Hirsute.
- *Leaf zonation color.*—RHS 187B.
- *Color of veins, upper surface.*—RHS 137A, largely indistinct.
- *Color of veins, lower surface.*—RHS 144B, becoming indistinct.
- *Pattern of veining.*—Palmate.
- *Petiole color.*—RHS 143B, slightly mottled close to RHS 176C.
- *Petiole length.*—5-6.5 cm.
- *Diameter of petiole.*—0.2 cm.
- *Texture.*—Pilose, hirsute, glandular hairs.

Stem:
- *Quantity of branches.*—5-9.
- *Color of stem.*—Close to RHS 143C.
- *Anthocyanin coloration of stem.*—A weak anthocyanin coloration is visible towards the top of the stem.
- *Length of stem.*—5-17 cm.
- *Diameter.*—1.0 cm.
- *Length of internodes.*—1-4 cm.
- *Texture.*—Sparsely hirsute, pilose, glandular hairs.

Peduncle:
- *Color of peduncle.*—RHS 137B.
- *Length of peduncle.*—9-12 cm.
- *Peduncle diameter.*—0.2-0.3 cm.
- *Texture.*—Hirsute, glandular hairs.
- *Anthocyanin coloration of peduncle.*—Strong coloring, RHS 187A.

Pedicel:
- *Color of pedicel.*—RHS 187A.
- *Length of pedicel.*—3.5-4 cm.
- *Diameter of pedicel.*—0.2 cm.
- *Texture.*—Sparsely pilose, glandular hairs.
- *Pedicel swelling.*—Swelling was not observed.

Bud (just before opening):
- *Color.*—RHS 75D.
- *Length.*—2.3 cm.
- *Width.*—0.6-0.7 cm.
- *Shape.*—Elliptical.

Inflorescence:
- *Type.*—Umbel; semi-spherical or nearly semi-spherical.
- *Lastingness of individual flowers.*—7-9 days at 18° C. temperature.
- *Number of inflorescences per plant.*—6-12, with 5-12 immature umbels in various stages.
- *Average total number of buds.*—8.
- *Fragrance.*—None.
- *Umbel diameter.*—8-10 cm.
- *Umbel depth.*—6-7 cm.

Corolla:
- *Form.*—Single.
- *Number of petals.*—5.
- *Diameter of flower.*—4.5-5 cm.
- *Depth of flower.*—1-1.5 cm.
- *Side view shape.*—Flat.
- *Color upper petals, upper surface.*—RHS 75D at anthesis, ageing to RHS N74B edged RHS 75B at anthesis.
- *Color upper petals, lower surface.*—RHS 75D, veins RHS 75B.
- *Length of upper petals.*—2.5-2.7 cm.
- *Width of upper petals.*—1.8-1.9 cm.
- *Color lower petals, upper surface.*—RHS 75D at anthesis, ageing to RHS N74B edged RHS 75B at anthesis.
- *Color lower petals, lower surface.*—RHS 75D, veins RHS 75B.
- *Markings on upper petals.*—Veins RHS N74A spot RHS 67C.
- *Markings on lower petals.*—Veins at anthesis RHS 75B.
- *Length of lower petals.*—2.4-2.6 cm.
- *Width of lower petals.*—1.8-2.2 cm.
- *Petal shape.*—Obovate to spathulate.
- *Apex shape.*—Rounded.
- *Margin.*—Entire.
- *Base.*—Attenuate.
- *Petal texture.*—Papillose on both surfaces.

Calyx:
- *Number of sepals.*—5.
- *Color of sepals.*—RHS 187A.
- *Length of sepals.*—1.3-1.4 cm.
- *Width of sepals.*—0.3-0.5 cm.
- *Sepal shape.*—Lanceolate to linear.
- *Apex shape.*—Acute.
- *Margins.*—Mostly fused.
- *Texture, upper surface.*—Glabrous.
- *Lower surface.*—Glandular hairs, hirsute.

*Sepal flexing*.—Mostly unflexed sepals. The narrowest sepals might flex moderately.

Reproductive organs:

Gynoecium:

*Pistil length*.—0.9 cm.

*Style color*.—RHS 71B.

*Style length*.—0.3 cm.

*Stigma color*.—RHS 71D.

*Ovary color*.—RHS 187B.

*Ovary length*.—0.5 cm.

*Ovary diameter*.—0.2 cm.

Androecium:

*Number of stamens*.—5 with 2 staminoids.

*Color of filaments*.—RHS N155A coloring towards apex RHS 72D.

*Length filaments*.—0.5-0.6 cm.

*Anther color*.—RHS N66C.

*Length of anthers*.—0.2-0.3 cm.

*Color of pollen*.—RHS NN167A.

*Pollen amount*.—Scarce.

*Fertility/seed set*.—Has not been determined to date.

*Disease/pest resistance*.—Has not been determined to date.

What is claimed is:

1. A new and distinct variety of *Pelargonium* plant named 'PEQZ0097' substantially as illustrated and described herein.

* * * * *